(12) United States Patent
Tonomura et al.

(10) Patent No.: US 8,436,166 B2
(45) Date of Patent: May 7, 2013

(54) AMINO-CONTAINING VINYLSILANE COMPOUNDS AND MAKING METHOD

(75) Inventors: Yoichi Tonomura, Joetsu (JP); Tohru Kubota, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 305 days.

(21) Appl. No.: 12/797,721

(22) Filed: Jun. 10, 2010

(65) Prior Publication Data

US 2010/0317852 A1    Dec. 16, 2010

(30) Foreign Application Priority Data

Jun. 15, 2009  (JP) ................................. 2009-142049

(51) Int. Cl.
*C07F 7/10*    (2006.01)
(52) U.S. Cl.
USPC ............................. 544/229; 556/481; 556/465
(58) Field of Classification Search .................. 544/229; 556/481, 465
See application file for complete search history.

(56) References Cited

U.S. PATENT DOCUMENTS 3,853,994 A    12/1974   Barcza

FOREIGN PATENT DOCUMENTS

| EP | 0 524 829 A1 | 1/1993 |
|---|---|---|
| JP | 02-270889 A | 11/1990 |
| JP | 04-149183 A | 5/1992 |
| JP | 7-228734 A | 8/1995 |
| JP | 2003-073503 A | 3/2003 |
| JP | 2004-099632 A | 4/2004 |

OTHER PUBLICATIONS

Japanese Office Action dated Nov. 9, 2011, issued in corresponding Japanese Patent Application No. 2009-142049.
Nagasaki Yukio. et al.; "Novel Synthesis of a Macromonomer Having Organosilyl and Amino Groups"; Journal of Macromolecular Science, Pure and Applied Chemistry, 1992, vol. A29, No. 6, pp. 457-470.
European Search Report Dec. 10, 2010, issued in corresponding European Patent Application No. 10006144.9.
Grobe, J. et al.; "Zur Addition von Dimethylamin und Dimethylphosphin an Vinylsilane", Journal of Organometallic Chemistry, vol. 17, No. 2, May 1969, pp. 263-275, XP007916065.
Nagasaki, Yukio et al.; "Reactivity of Lithium Alkylamide toward Vinylsilane Derivatives"; Bulletin of The Chemical Society of Japan, vol. 65, No. 4, 2006, pp. 949-953, XP007916066.
Unkelbach, Christian et al.; "Low-Temperature Addition of Organolithiums to Functionalized Vinylsilanes under Formation of Secondary alpha-Lithiated Alkylsilanes"; Journal of the American Chemical Society, vol. 131, No. 47, Dec. 2, 2009, pp. 17044-17045, XP009141968.

*Primary Examiner* — Kristin Bianchi
(74) *Attorney, Agent, or Firm* — Westerman, Hattori, Daniels & Adrian, LLP

(57) ABSTRACT

Vinylsilane compounds having a specific amino group, typically diethylaminopropyldimethylvinylsilane, N-methylpiperazinylpropyldimethylvinylsilane, and bistrimethylsilylaminopropyldimethylvinylsilane are novel and useful as a modifier for polymers.

5 Claims, 6 Drawing Sheets

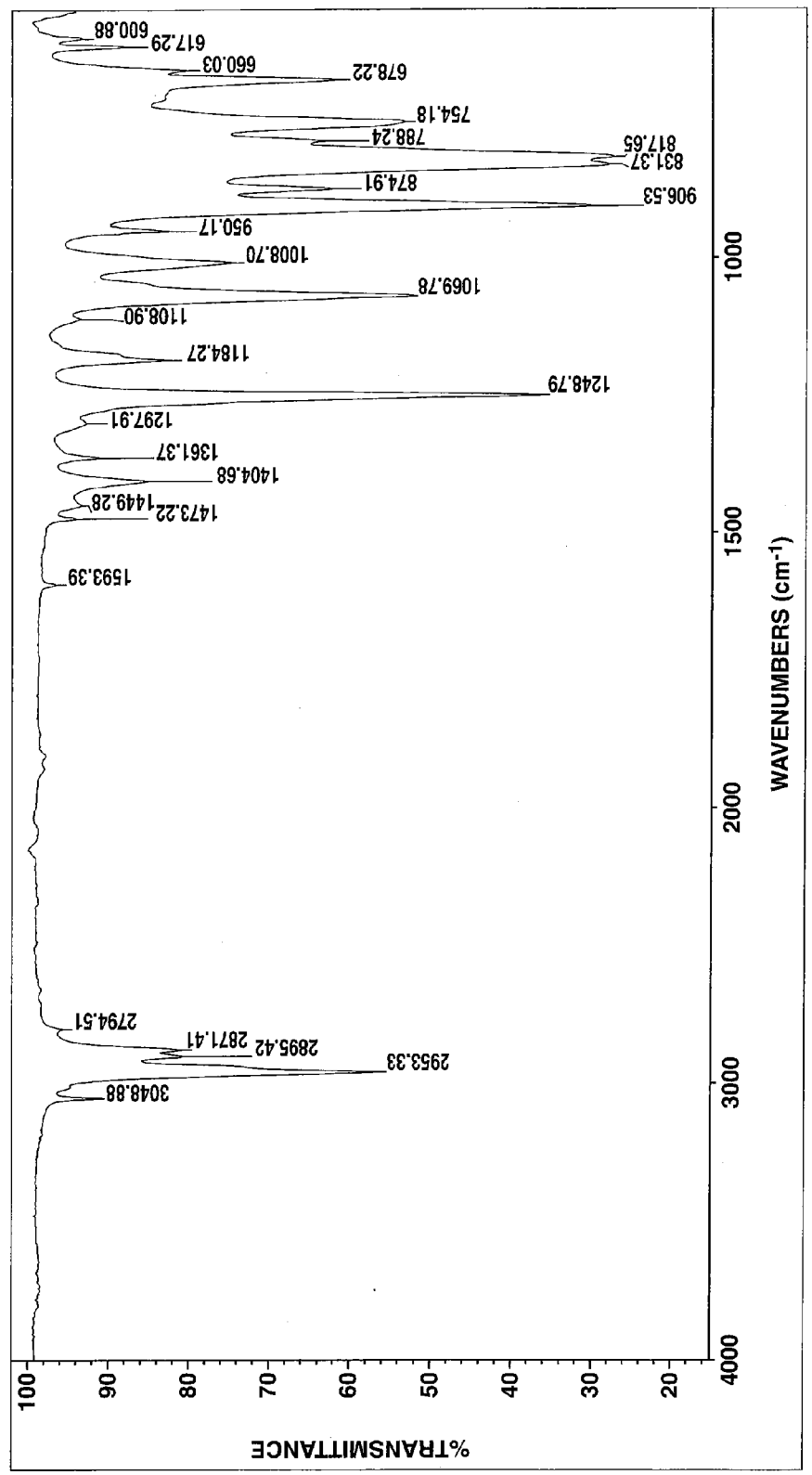

AMINO-CONTAINING VINYLSILANE COMPOUNDS AND MAKING METHOD

CROSS-REFERENCE TO RELATED APPLICATION

This non-provisional application claims priority under 35 U.S.C. §119(a) on Patent Application No. 2009-142049 filed in Japan on Jun. 15, 2009, the entire contents of which are hereby incorporated by reference.

TECHNICAL FIELD

This invention relates to novel amino-containing vinylsilane compounds useful as a polymer modifier and a method for preparing the same.

BACKGROUND ART

While a number of attempts have been made to improve polymer properties, one typical attempt is by introducing functional groups into polymers.

One of such functional group introduction methods is modification of polymers using compounds having a polar group and a double bond. Exemplary methods include modification of polyolefin with maleic anhydride as disclosed in JP-A 2004-99632; modification of polyolefin with a N-vinylalkylamide compound as disclosed in JP-A H07-228734; and modification of a thermoplastic elastomer with an acrylamide compound as disclosed in JP-A 2003-73503.

These modification methods are successful in improving properties of polymers. For example, the modification of polyolefin with maleic anhydride described in JP-A 2004-99632 results in a polyolefin having a good balance of melt tension and fluidity. The N-vinylalkylamide-modified polyolefin described in JP-A H07-228734 has a good balance of rigidity and impact resistance. The acrylamide-modified thermoplastic elastomer described in JP-A 2003-73503 is an elastomer having improved tensile properties.

As the intended use of polymers is diversified, it would be desirable to have a polymer with further improved properties. There exists a need for a modifier capable of modification to improve polymer properties.

Citation List

Patent Document 1: JP-A 2004-99632

Patent Document 2: JP-A H07-228734

Patent Document 3: JP-A 2003-73503

DISCLOSURE OF INVENTION

An object of the invention is to provide an amino-containing vinylsilane compound which is useful as a modifier for effectively modifying polymers to improve their properties, and a method for preparing the same.

The inventors have found that vinylsilane compounds having a specific amino group as represented by the general formula (1) below are useful as a modifier capable of effectively modifying polymers to improve their properties.

In one aspect, the invention provides an amino-containing vinylsilane compound having the general formula (1):

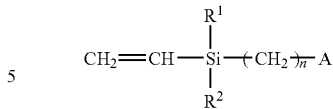

wherein $R^1$ and $R^2$ are each independently a monovalent hydrocarbon group of 1 to 10 carbon atoms, A is a group of the general formula (2):

$$—NR^3R^4 \quad (2)$$

wherein $R^3$ and $R^4$ are each independently a monovalent hydrocarbon group of 1 to 10 carbon atoms or triorganosilyl group of 3 to 40 carbon atoms, or the general formula (3):

wherein E is $—CH_2—$, $—O—$ or $—NR^5—$, $R^5$ is a monovalent hydrocarbon group of 1 to 10 carbon atoms or triorganosilyl group of 3 to 40 carbon atoms, and n is an integer of 1 to 10.

In another aspect, the invention provides a method for preparing an amino-containing vinylsilane compound of formula (1), comprising the step of reacting a vinylsilane compound having the general formula (4):

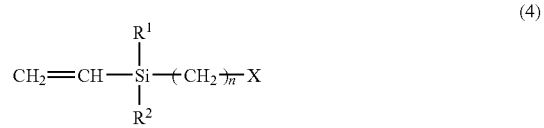

wherein $R^1$ and $R^2$ are each independently a monovalent hydrocarbon group of 1 to 10 carbon atoms, X is chlorine, bromine or iodine, and n is an integer of 1 to 10 with an amine compound having the general formula (5):

$$H-A \quad (5)$$

wherein A is a group of the general formula (2):

$$—NR^3R^4 \quad (2)$$

wherein $R^3$ and $R^4$ are each independently a monovalent hydrocarbon group of 1 to 10 carbon atoms or triorganosilyl group of 3 to 40 carbon atoms, or the general formula (3):

wherein E is $—CH_2—$, $—O—$ or $—NR^5—$, $R^5$ is a monovalent hydrocarbon group of 1 to 10 carbon atoms or triorganosilyl group of 3 to 40 carbon atoms.

Preferably, the reaction occurs at a temperature of −20° C. to 200° C. using 1 mole of the vinylsilane compound of formula (4) and 0.5 to 5.0 moles of the amine compound of formula (5).

In a further aspect, the invention provides a method for preparing an amino-containing vinylsilane compound of formula (1), comprising the steps of reacting an amine compound having the general formula (6):

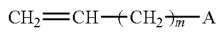  (6)

wherein A is a group of the general formula (2):

—NR³R⁴  (2)

wherein R³ and R⁴ are each independently a monovalent hydrocarbon group of 1 to 10 carbon atoms or triorganosilyl group of 3 to 40 carbon atoms, or the general formula (3):

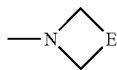  (3)

wherein E is —CH₂—, —O— or —NR⁵—, R⁵ is a monovalent hydrocarbon group of 1 to 10 carbon atoms or triorganosilyl group of 3 to 40 carbon atoms, and m is an integer of 0 to 8, with a hydrogensilane compound having the general formula (7):

HSiR¹R²Y  (7)

wherein R¹ and R² are each independently a monovalent hydrocarbon group of 1 to 10 carbon atoms, Y is an organoxy group of 1 to 10 carbon atoms, chlorine, bromine or iodine, in the presence of a platinum catalyst, to form an amino-containing silane compound having the general formula (8):

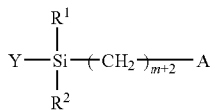  (8)

wherein R¹, R², A, Y and m are as defined above, and reacting the amino-containing silane compound with a vinyl Grignard reagent.

Preferably, the reaction occurs at a temperature of −20° C. to 200° C. using 1 mole of the amine compound of formula (6), 0.5 to 3.0 moles of the hydrogensilane compound of formula (7), 0.5 to 3.0 moles of the vinyl Grignard reagent, and 0.000001 to 0.01 mole of the platinum catalyst.

Advantageous Effects of Invention

The amino-containing vinylsilane compounds of the invention are useful as a polymer modifier or the like since polymers can be modified with the compounds to attain significant improvements in polymer properties.

BRIEF DESCRIPTION OF DRAWINGS

FIGS. 5 and 6 are ¹H-NMR and IR spectra of bistrimethylsilylaminopropyldimethylvinylsilane in Example 3, respectively.

DESCRIPTION OF EMBODIMENTS

Figure 1:
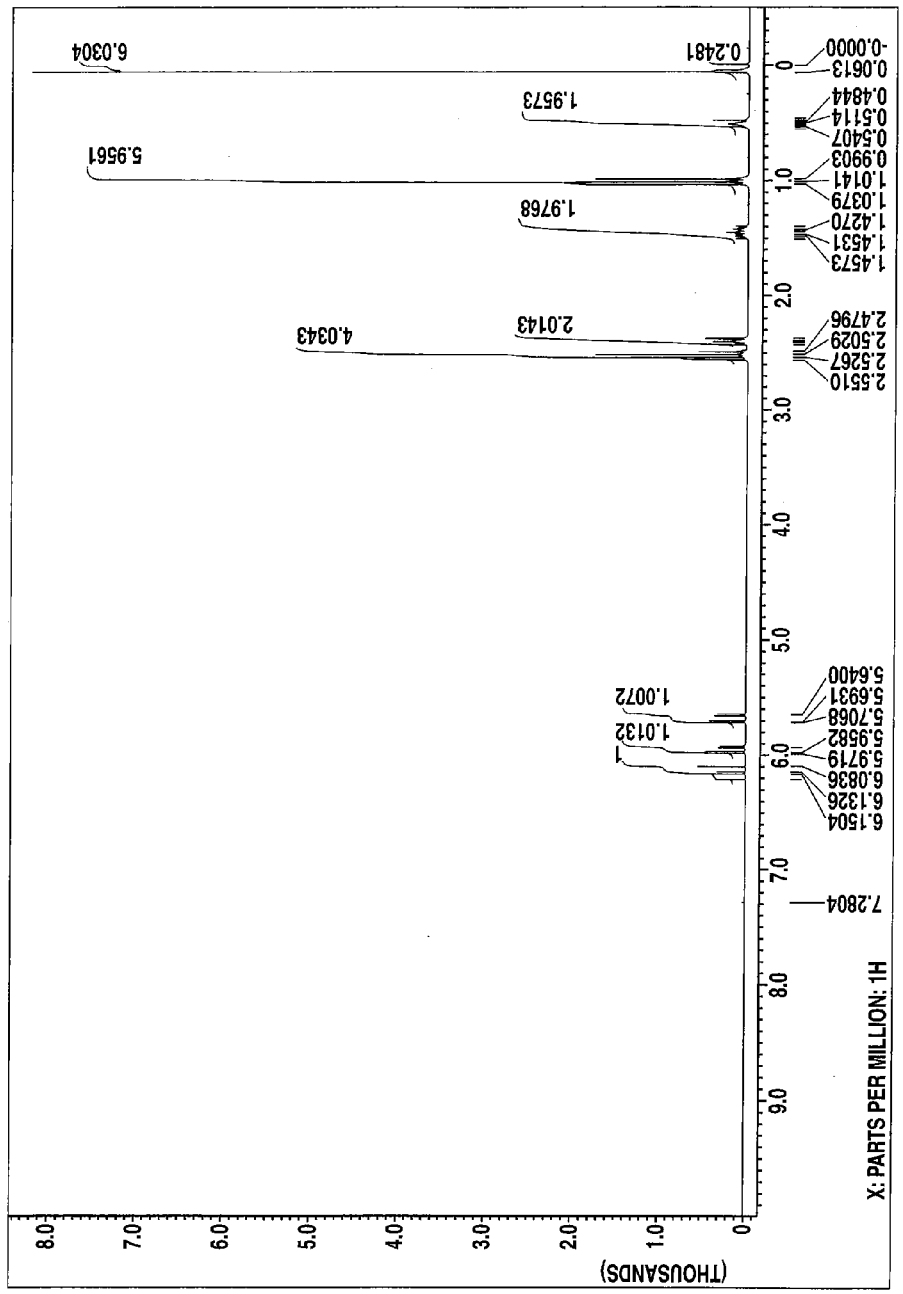
FIGS. 1 and 2 are ¹H-NMR and IR spectra of diethylaminopropyldimethylvinylsilane in Example 1, respectively.

The amino-containing vinylsilane compounds of the invention have the general formula (1).

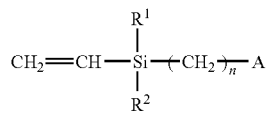  (1)

Herein R¹ and R² are each independently a monovalent hydrocarbon group of 1 to 10 carbon atoms. A is a group of the general formula (2):

—NR³R⁴  (2)

wherein R³ and R⁴ are each independently a monovalent hydrocarbon group of 1 to 10 carbon atoms or a triorganosilyl group of 3 to 40 carbon atoms, or the general formula (3):

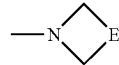  (3)

wherein E is —CH₂—, —O— or —NR⁵—, R⁵ is a monovalent hydrocarbon group of 1 to 10 carbon atoms or a triorganosilyl group of 3 to 40 carbon atoms, alone or a combination of two or more of these groups. The subscript n is an integer of 1 to 10.

Examples of the monovalent hydrocarbon group of 1 to 10 carbon atoms represented by R¹, R², R³, R⁴ and R⁵ include, but are not limited to, methyl, ethyl, propyl, isopropyl, butyl, isobutyl, sec-butyl, tert-butyl, pentyl, hexyl, heptyl, octyl, 2-ethylhexyl, nonyl, decyl, cyclopropyl, cyclobutyl, cyclopentyl, cyclohexyl, norbornyl, phenyl, tolyl, and benzyl.

Examples of the triorganosilyl group of 3 to 40 carbon atoms represented by R³, R⁴ and R⁵ include, but are not limited to, trimethylsilyl, ethyldimethylsilyl, vinyldimethylsilyl, ethynyldimethylsilyl, diethylmethylsilyl, propyldimethylsilyl, isopropyldimethylsilyl, cyclopropyldimethylsilyl, allyldimethylsilyl, butyldimethylsilyl, isobutyldimethylsilyl, t-butyldimethylsilyl, cyclobutyldimethylsilyl, sec-butyldimethylsilyl, triethylsilyl, trivinylsilyl, pentyldimethylsilyl, cyclopentyldimethylsilyl, methyldiisopropylsilyl, isopropyldiethylsilyl, hexyldimethylsilyl, cyclohexyldimethylsilyl, cyclohexenyldimethylsilyl, thexyldimethylsilyl, 1-methylcyclopentyldimethylsilyl, phenyldimethylsilyl, butyldiethylsilyl, heptyldimethylsilyl, cycloheptyldimethylsilyl, 2-norbornyldimethylsilyl, 5-norbornen-2-yldimethylsilyl, tolyldimethylsilyl, benzyldimethylsilyl, triisopropylsilyl, octyldimethylsilyl, hexyldiethylsilyl, decyldimethylsilyl, tributylsilyl, triisobutylsilyl, dodecyldimethylsilyl, tetradecyldimethylsilyl, hexadecyldimethylsilyl, octadecyldimethylsilyl, and eicosyldimethylsilyltrimethylsilyl.

Examples of the amino-containing vinylsilane compounds having formula (1) include, but are not limited to, dimethylaminomethyldimethylvinylsilane, diethylaminomethyldimethylvinylsilane, dipropylaminomethyldimethylvinylsilane, diisopropylaminomethyldimethylvinylsilane, dibuylaminomethyldimethylvinylsilane, diisobutylaminomethyldimethylvinylsilane, di(sec-butyl)aminomethyldimethylvinylsilane, diphenylaminomethyldimethylvinylsilane, dicyclopentylaminomethyldimethylvinylsilane, dicyclohexylaminomethyldimethylvinylsilane, dibenzylaminomethyldimethylvinylsilane, pyrrolidinylmethyldimethylvinylsilane, piperidinylmethyldimethylvinylsilane, N-methylpiperazinylmethyldimethylvinylsilane, N-ethylpiperazinylmethyldimethylvinylsilane, morpholinylmethyldimethylvinylsilane, N,N-bistrimethylsilylaminomethyldimethylvinylsilane, trimethylsilylmethylaminomethyldimethylvinylsilane, trimethylsilylethylaminomethyldimethylvinylsilane, trimethylsilylpropylaminomethyldimethylvinylsilane, trimethylsilylisopropylaminomethyldimethylvinylsilane, trimethylsilylbutylaminomethyldimethylvinylsilane, trimethylsilyl-sec-butylaminomethyldimethylvinylsilane, trimethylsilylphenylaminomethyldimethylvinylsilane, trimethylsilylcyclopentylaminomethyldimethylvinylsilane, trimethylsilylcyclohexylaminomethyldimethylvinylsilane, triethylsilylmethylaminomethyldimethylvinylsilane, triethylsilylethylaminomethyldimethylvinylsilane, triethylsilylpropylaminomethyldimethylvinylsilane, triethylsilylisopropylaminomethyldimethylvinylsilane, triethylsilylbutylaminomethyldimethylvinylsilane, triethylsilyl-sec-butylaminomethyldimethylvinylsilane, triethylsilylphenylaminomethyldimethylvinylsilane, triethylsilylcyclopentylaminomethyldimethylvinylsilane, triethylsilylcyclohexylaminomethyldimethylvinylsilane, t-butyldimethylsilylmethylaminomethyldimethylvinylsilane, t-butyldimethylsilylethylaminomethyldimethylvinylsilane, t-butyldimethylsilylpropylaminomethyldimethylvinylsilane, t-butyldimethylsilylisopropylaminomethyldimethylvinylsilane, t-butyldimethylsilylbutylaminomethyldimethylvinylsilane, t-butyldimethylsilyl-sec-butylaminomethyldimethylvinylsilane, t-butyldimethylsilylphenylaminomethyldimethylvinylsilane, t-butyldimethylsilylcyclopentylaminomethyldimethylvinylsilane, t-butyldimethylsilylcyclohexylaminomethyldimethylvinylsilane, triisopropylsilylmethylaminomethyldimethylvinylsilane, triisopropylsilylethylaminomethyldimethylvinylsilane, triisopropylsilylpropylaminomethyldimethylvinylsilane, triisopropylsilylisopropylaminomethyldimethylvinylsilane, triisopropylsilylbutylaminomethyldimethylvinylsilane, triisopropylsilyl-sec-butylaminomethyldimethylvinylsilane, triisopropylsilylphenylaminomethyldimethylvinylsilane, triisopropylsilylcyclopentylaminomethyldimethylvinylsilane, triisopropylsilylcyclohexylaminomethyldimethylvinylsilane, N-trimethylsilylpiperazinylmethyldimethylvinylsilane, N-triethylsilylpiperazinylmethyldimethylvinylsilane, N-t-butyldimethylsilylpiperazinylmethyldimethylvinylsilane, N-triisopropylsilylpiperazinylmethyldimethylvinylsilane, dimethylaminoethyldimethylvinylsilane, diethylaminoethyldimethylvinylsilane, dipropylaminoethyldimethylvinylsilane, diisopropylaminoethyldimethylvinylsilane, dibutylaminoethyldimethylvinylsilane, diisobutylaminoethyldimethylvinylsilane, di(sec-butyl)aminoethyldimethylvinylsilane, diphenylaminoethyldimethylvinylsilane, dicyclopentylaminoethyldimethylvinylsilane, dicyclohexylaminoethyldimethylvinylsilane, dibenzylaminoethyldimethylvinylsilane, pyrrolidinylethyldimethylvinylsilane, piperidinylethyldimethylvinylsilane, N-methylpiperazinylethyldimethylvinylsilane, N-ethylpiperazinylethyldimethylvinylsilane, morpholinylethyldimethylvinylsilane, N,N-bistrimethylsilylaminoethyldimethylvinylsilane, trimethylsilylmethylaminoethyldimethylvinylsilane, trimethylsilylethylaminoethyldimethylvinylsilane, trimethylsilylpropylaminoethyldimethylvinylsilane, trimethylsilylisopropylaminoethyldimethylvinylsilane, trimethylsilylbutylaminoethyldimethylvinylsilane, trimethylsilyl-sec-butylaminoethyldimethylvinylsilane, trimethylsilylphenylaminoethyldimethylvinylsilane, trimethylsilylcyclopentylaminoethyldimethylvinylsilane, trimethylsilylcyclohexylaminoethyldimethylvinylsilane, triethylsilylmethylaminoethyldimethylvinylsilane, triethylsilylethylaminoethyldimethylvinylsilane, triethylsilylpropylaminoethyldimethylvinylsilane, triethylsilylisopropylaminoethyldimethylvinylsilane, triethylsilylbutylaminoethyldimethylvinylsilane, triethylsilyl-sec-butylaminoethyldimethylvinylsilane, triethylsilylphenylaminoethyldimethylvinylsilane, triethylsilylcyclopentylaminoethyldimethylvinylsilane, triethylsilylcyclohexylaminoethyldimethylvinylsilane, t-butyldimethylsilylmethylaminoethyldimethylvinylsilane, t-butyldimethylsilylethylaminoethyldimethylvinylsilane, t-butyldimethylsilylpropylaminoethyldimethylvinylsilane, t-butyldimethylsilylisopropylaminoethyldimethylvinylsilane, t-butyldimethylsilylbutylaminoethyldimethylvinylsilane, t-butyldimethylsilyl-sec-butylaminoethyldimethylvinylsilane, t-butyldimethylsilylphenylaminoethyldimethylvinylsilane, t-butyldimethylsilylcyclopentylaminoethyldimethylvinylsilane, t-butyldimethylsilylcyclohexylaminoethyldimethylvinylsilane, triisopropylsilylmethylaminoethyldimethylvinylsilane, triisopropylsilylethylaminoethyldimethylvinylsilane, triisopropylsilylpropylaminoethyldimethylvinylsilane, triisopropylsilylisopropylaminoethyldimethylvinylsilane, triisopropylsilylbutylaminoethyldimethylvinylsilane, triisopropylsilyl-sec-butylaminoethyldimethylvinylsilane, triisopropylsilylphenylaminoethyldimethylvinylsilane, triisopropylsilylcyclopentylaminoethyldimethylvinylsilane, triisopropylsilylcyclohexylaminoethyldimethylvinylsilane, N-trimethylsilylpiperazinylethyldimethylvinylsilane, N-triethylsilylpiperazinylethyldimethylvinylsilane, N-t-butyldimethylsilylpiperazinylethyldimethylvinylsilane, N-triisopropylsilylpiperazinylethyldimethylvinylsilane, dimethylaminopropyldimethylvinylsilane, diethylaminopropyldimethylvinylsilane, dipropylaminopropyldimethylvinylsilane, diisopropylaminopropyldimethylvinylsilane, dibutylaminopropyldimethylvinylsilane, diisobutylaminopropyldimethylvinylsilane, di(sec-butyl)aminopropyldimethylvinylsilane, diphenylaminopropyldimethylvinylsilane, dicyclopentylaminopropyldimethylvinylsilane, dicyclohexylaminopropyldimethylvinylsilane, dibenzylaminopropyldimethylvinylsilane, pyrrolidinylpropyldimethylvinylsilane, piperidinylpropyldimethylvinylsilane, N-methylpiperazinylpropyldimethylvinylsilane, N-ethylpiperazinylpropyldimethylvinylsilane, morpholinylpropyldimethylvinylsilane, N,N-bistrimethylsilylaminopropyldimethylvinylsilane, trimethylsilylmethylaminopropyldimethylvinylsilane, trimethylsilylethylaminopropyldimethylvinylsilane, trimethylsilylpropylaminopropyldimethylvinylsilane, trimethylsilylisopropylaminopropyldimethylvinylsilane, trimethylsilylbutylaminopropyldimethylvinylsilane, trimethylsilyl-sec-butylaminopropyldimethylvinylsilane, trimethylsilylphenylaminopropyldimethylvinylsilane, trimethylsilylcyclopentylaminopropyldimethylvinylsilane, trimethylsilylcyclohexylaminopropyldimethylvinylsilane, triethylsilylmethylaminopropyldimethylvinylsilane, triethylsilylethylaminopropyldimethylvinylsilane, triethylsilylpropylaminopropyldimethylvinylsilane, triethylsilylisopropylaminopropyldimethylvinylsilane, triethylsilylbutylaminopropyldimethylvinylsilane, triethylsilyl-sec-butylaminopropyldimethylvinylsilane, triethylsilylphenylaminopropyldimethylvinylsilane, triethylsilylcyclopentylaminopropyldimethylvinylsilane, triethylsilylcyclohexylaminopropyldimethylvinylsilane, t-butyldimethylsilylmethylaminopropyldimethylvinylsilane, t-butyldimethylsilylethylaminopropyldimethylvinylsilane, t-butyldimethylsilylpropylaminopropyldimethylvinylsilane, t-butyldimethylsilylisopropylaminopropyldimethylvinylsilane, t-butyldimethylsilylbutylaminopropyldimethylvinylsilane, t-butyldimethylsilyl-sec-butylaminopropyldimethylvinylsilane, t-butyldimethylsilylphenylaminopropyldimethylvinylsilane, t-butyldimethylsilylcyclopentylaminopropyldimethylvinylsilane, t-butyldimethylsilylcyclohexylaminopropyldimethylvinylsilane, triisopropylsilylmethylaminopropyldimethylvinylsilane, triisopropylsilylethylaminopropyldimethylvinylsilane, triisopropylsilylpropylaminopropyldimethylvinylsilane, triisopropylsilylisopropylaminopropyldimethylvinylsilane, triisopropylsilylbutylaminopropyldimethylvinylsilane, triisopropylsilyl-sec-butylaminopropyldimethylvinylsilane, triisopropylsilylphenylaminopropyldimethylvinylsilane, triisopropylsilylcyclopentylaminopropyldimethylvinylsilane, triisopropylsilylcyclohexylaminopropyldimethylvinylsilane, N-trimethylsilylpiperazinylpropyldimethylvinylsilane, N-triethylsilylpiperazinylpropyldimethylvinylsilane, N-t-butyldimethylsilylpiperazinylpropyldimethylvinylsilane, N-triisopropylsilylpiperazinylpropyldimethylvinylsilane, etc.

In one embodiment, the amino-containing vinylsilane compound of formula (1) is prepared by reacting a vinylsilane compound having the general formula (4):

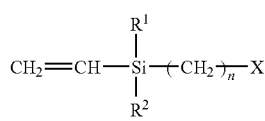

(4)

wherein $R^1$ and $R^2$ are each independently a monovalent hydrocarbon group of 1 to 10 carbon atoms, X is a chlorine, bromine or iodine atom, and n is an integer of 1 to 10 with an amine compound having the general formula (5):

H-A     (5)

wherein A is a group of the general formula (2):

—$NR^3R^4$     (2)

wherein $R^3$ and $R^4$ are each independently a monovalent hydrocarbon group of 1 to 10 carbon atoms or triorganosilyl group of 3 to 40 carbon atoms, or the general formula (3):

(3)

wherein E is —$CH_2$—, —O— or —$NR^5$—, and $R^5$ is a monovalent hydrocarbon group of 1 to 10 carbon atoms or triorganosilyl group of 3 to 40 carbon atoms.

Groups $R^1$ and $R^2$ in formula (4) and $R^3$, $R^4$ and $R^5$ in formula (5) are as exemplified above.

In the reaction, the vinylsilane compound of formula (4) and the amine compound of formula (5) may be combined in any desired ratio. From the standpoints of reactivity and productivity, it is preferred to use 0.5 to 5.0 moles, more preferably 0.8 to 3.0 moles of the amine compound per mole of the vinylsilane compound.

The reaction of the vinylsilane compound with the amine compound forms hydrogen halide as a by-product, which may be trapped using the amine compound of formula (5) itself as a base or another amine compound as a base. The amine compounds which can be used for trapping include trimethylamine, triethylamine, tripropylamine, tributylamine, ethyldiisopropylamine, pyridine, dimethylaminopyridine, dimethylaniline, methylimidazole, tetramethylethylenediamine, and 1,8-diazabicyclo[5.4.0]undecene-7 as well as the amine compounds of formula (5). In this regard, although the vinylsilane compound of formula (4) and the amine compound of formula (5) may be combined in any desired ratio, it is preferred from the standpoints of reactivity and productivity to use 0.5 to 5.0 moles, more preferably 0.8 to 3.0 moles of the amine compound per mole of the vinylsilane compound when the hydrogen halide is trapped using the amine compound of formula (5) itself as a base, or to use 0.2 to 2.0 moles, more preferably 0.3 to 1.5 moles of the amine compound per mole of the vinylsilane compound when the hydrogen halide is trapped using another amine compound as a base.

When the hydrogen halide is trapped using another amine compound as a base, the amount of the other amine compound used is not particularly limited. It is preferred from the standpoints of reactivity and productivity to use 0.3 to 3.0 moles, more preferably 0.5 to 1.5 moles of the other amine compound per mole of the vinylsilane compound.

Although the reaction temperature is not particularly limited, the reaction preferably occurs at a temperature of –20° C. to 200° C., more preferably 0° C. to 150° C. and atmospheric pressure or added pressure.

A solvent may be used although the reaction may take place in a solventless system. Suitable solvents include hydrocarbons such as pentane, hexane, cyclohexane, isooctane, benzene, toluene, and xylene, ethers such as diethyl ether, tetrahydrofuran, and dioxane, esters such as ethyl acetate and butyl acetate, ketones such as acetone, methyl ethyl ketone, and methyl isobutyl ketone, aprotic polar solvents such as acetonitrile, dimethyl sulfoxide, N,N-dimethylformamide, N-methylpyrrolidone, and hexamethylphosphoric triamide, alcohols such as methanol, ethanol, and isopropyl alcohol, and chlorinated hydrocarbons such as dichloromethane and chloroform. These solvents may be used alone or in admixture of two or more.

At the end of reaction, there forms a salt of the amine compound, which may be removed, for example, by filtering the reaction solution or by adding water, ethylenediamine or 1,8-diazabicyclo[5.4.0]undecene-7 to the reaction solution, followed by separation. Once the salt is removed from the reaction solution in this way, the target compound may be recovered from the reaction solution by standard techniques such as distillation.

In another embodiment, the amino-containing vinylsilane compound of formula (1) is prepared by reacting an amine compound having the general formula (6):

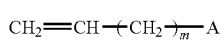

(6)

wherein A is a group of the general formula (2):

—$NR^3R^4$     (2)

wherein $R^3$ and $R^4$ are each independently a monovalent hydrocarbon group of 1 to 10 carbon atoms or triorganosilyl group of 3 to 40 carbon atoms, or the general formula (3):

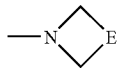  (3)

wherein E is —$CH_2$—, —O— or —$NR^5$—, $R^5$ is a monovalent hydrocarbon group of 1 to 10 carbon atoms or triorganosilyl group of 3 to 40 carbon atoms, and m is an integer of 0 to 8, with a hydrogensilane compound having the general formula (7):

$$HSiR^1R^2Y \quad (7)$$

wherein $R^1$ and $R^2$ are each independently a monovalent hydrocarbon group of 1 to 10 carbon atoms, Y is an organoxy group of 1 to 10 carbon atoms or a chlorine, bromine or iodine atom, in the presence of a platinum catalyst, to form an amino-containing silane compound having the general formula (8):

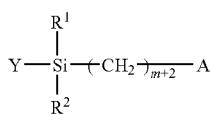  (8)

wherein $R^1$, $R^2$, A, Y and m are as defined above, and reacting the amino-containing silane compound with a vinyl Grignard reagent.

Groups $R^3$, $R^4$ and $R^5$ in formula (6) and $R^1$ and $R^2$ in formula (7) are as exemplified above.

Examples of the organoxy group of 1 to 10 carbon atoms represented by Y in formula (7) include, but are not limited to, methoxy, ethoxy, propoxy, isopropoxy, butoxy, isobutoxy, sec-butoxy, t-butoxy, pentyloxy, hexyloxy, heptyloxy, octyloxy, 2-ethylhexyloxy, nonyloxy, decyloxy, cyclopropoxy, cyclobutoxy, cyclopentyloxy, cyclohexyloxy, norbornyloxy, phenoxy, tolyloxy, and benzyloxy.

Examples of the vinyl Grignard reagent used herein include vinylmagnesium chloride, vinylmagnesium bromide, and vinylmagnesium iodide.

The amine compound of formula (6), the hydrogensilane compound of formula (7), and the vinyl Grignard reagent may be combined in any desired ratio. From the standpoints of reactivity and productivity, it is preferred to use 0.5 to 3.0 moles, more preferably 0.8 to 1.5 moles of the hydrogensilane compound and 0.5 to 3.0 moles, more preferably 0.8 to 1.5 moles of the vinyl Grignard reagent per mole of the amine compound.

Examples of the platinum catalyst used herein include chloroplatinic acid, chloroplatinic acid in alcohol, platinum-1,3-divinyl-1,1,3,3-tetramethyldisiloxane complex in toluene or xylene, tetrakistriphenylphosphine platinum, dichlorobistriphenylphosphine platinum, dichlorobisacetonitrile platinum, dichlorobisbenzonitrile platinum, and dichlorocyclooctadiene platinum.

The platinum catalyst may be used in any desired amount. From the standpoints of reactivity and productivity, it is preferred to use 0.000001 to 0.01 mole, more preferably 0.00001 to 0.001 mole of the platinum catalyst per mole of the amine compound of formula (6).

Although the reaction temperature is not particularly limited, the reactions preferably occur at a temperature of −20° C. to 200° C., more preferably 0° C. to 150° C. and atmospheric pressure or added pressure.

A solvent may be used although the reactions may take place in a solventless system. Suitable solvents include hydrocarbons such as pentane, hexane, cyclohexane, isooctane, benzene, toluene, and xylene, ethers such as diethyl ether, tetrahydrofuran, and dioxane, and chlorinated hydrocarbons such as dichloromethane and chloroform. These solvents may be used alone or in admixture of two or more.

EXAMPLE

Synthesis Examples and Examples of the invention are given below by way of illustration and not by way of limitation.

Synthesis Example 1

Synthesis of chloropropyldimethylvinylsilane

A flask equipped with a stirrer, reflux condenser, dropping funnel and thermometer was charged with 500 mL (0.73 mol) a tetrahydrofuran solution of 1.46M vinylmagnesium chloride, to which 119.8 g (0.7 mol) of chloropropyldimethylchlorosilane was added dropwise over 2 hours at an internal temperature of 25-50° C. The reaction solution was stirred for 2 hours. A salt formed was removed by filtration. By subsequent distillation, the target compound, chloropropyldimethylvinylsilane was collected as a fraction having a boiling point of 82° C./5 kPa in an amount of 104.4 g (yield 92%).

Example 1

Synthesis of diethylaminopropyldimethylvinylsilane

A flask equipped with a stirrer, reflux condenser, dropping funnel and thermometer was charged with 32.5 g (0.2 mol) of chloropropyldimethylvinylsilane and heated at 130° C. Once the internal temperature became constant, 30.0 g (0.41 mol) of diethylamine was added dropwise over 18 hours, followed by 10 hours of stirring. A hydrochloride salt formed was removed by filtration. By subsequent distillation, 29.7 g of a fraction having a boiling point of 81° C./1 kPa was collected.

The fraction was analyzed by mass, $^1$H-NMR and IR spectrometry, with the results shown below.

Figure 2:
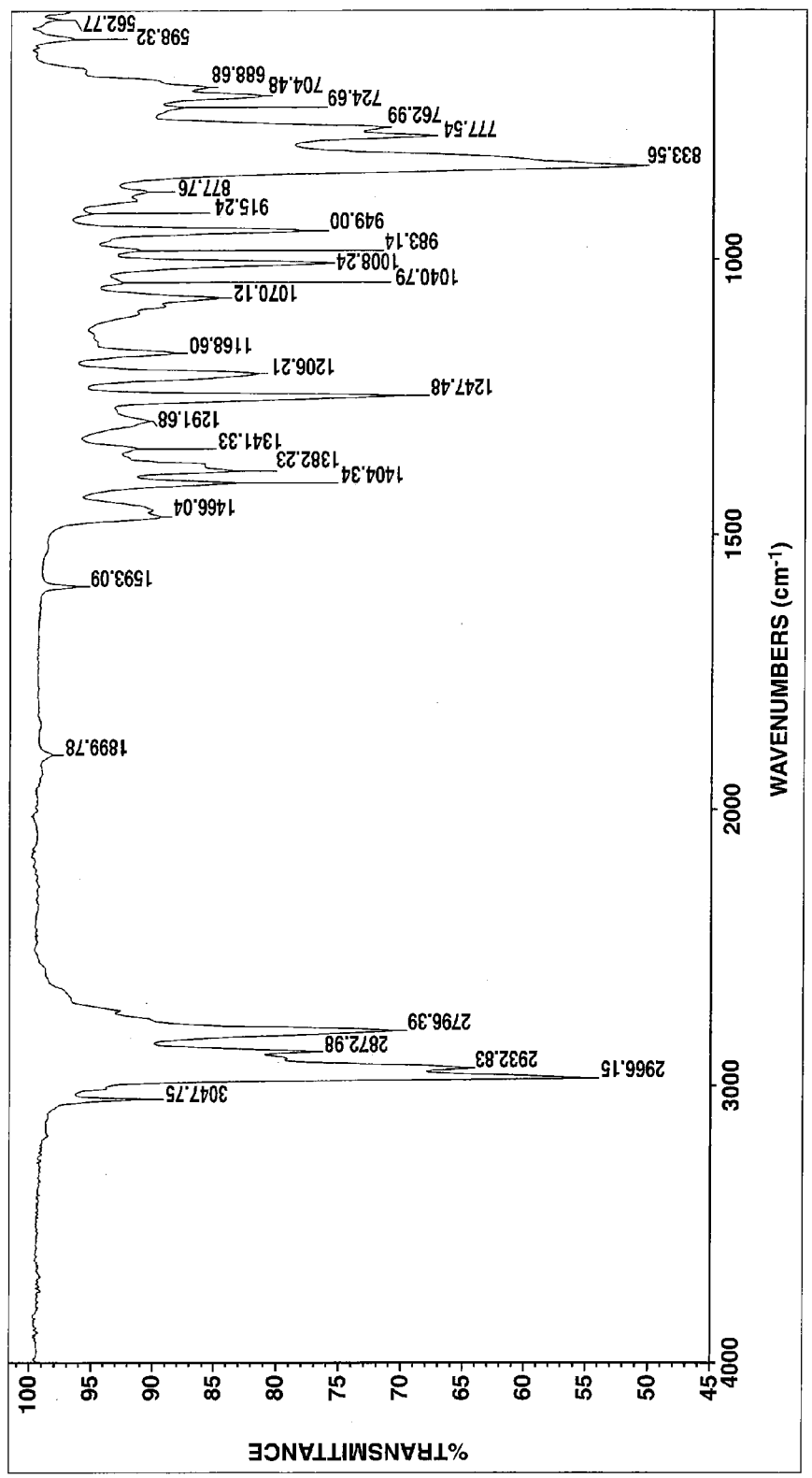

Mass spectrum
m/z 199, 184, 112, 86, 59
$^1$H-NMR spectrum (in heavy chloroform)
diagram of FIG. 1
IR spectrum
diagram of FIG. 2

With these data, the compound was identified to be diethylaminopropyldimethylvinylsilane.

Example 2

Synthesis of N-methylpiperazinylpropyldimethylvinylsilane

A flask equipped with a stirrer, reflux condenser, dropping funnel and thermometer was charged with 34.6 g (0.345 mol) of N-methylpiperazine and heated at 120° C. Once the internal temperature became constant, 24.4 g (0.15 mol) of chloropropyldimethylvinylsilane was added dropwise over 2 hours, followed by 6 hours of stirring. A hydrochloride salt formed was removed by filtration. By subsequent distillation, 28.4 g of a fraction having a boiling point of 106° C./0.4 kPa was collected.

Figure 3:
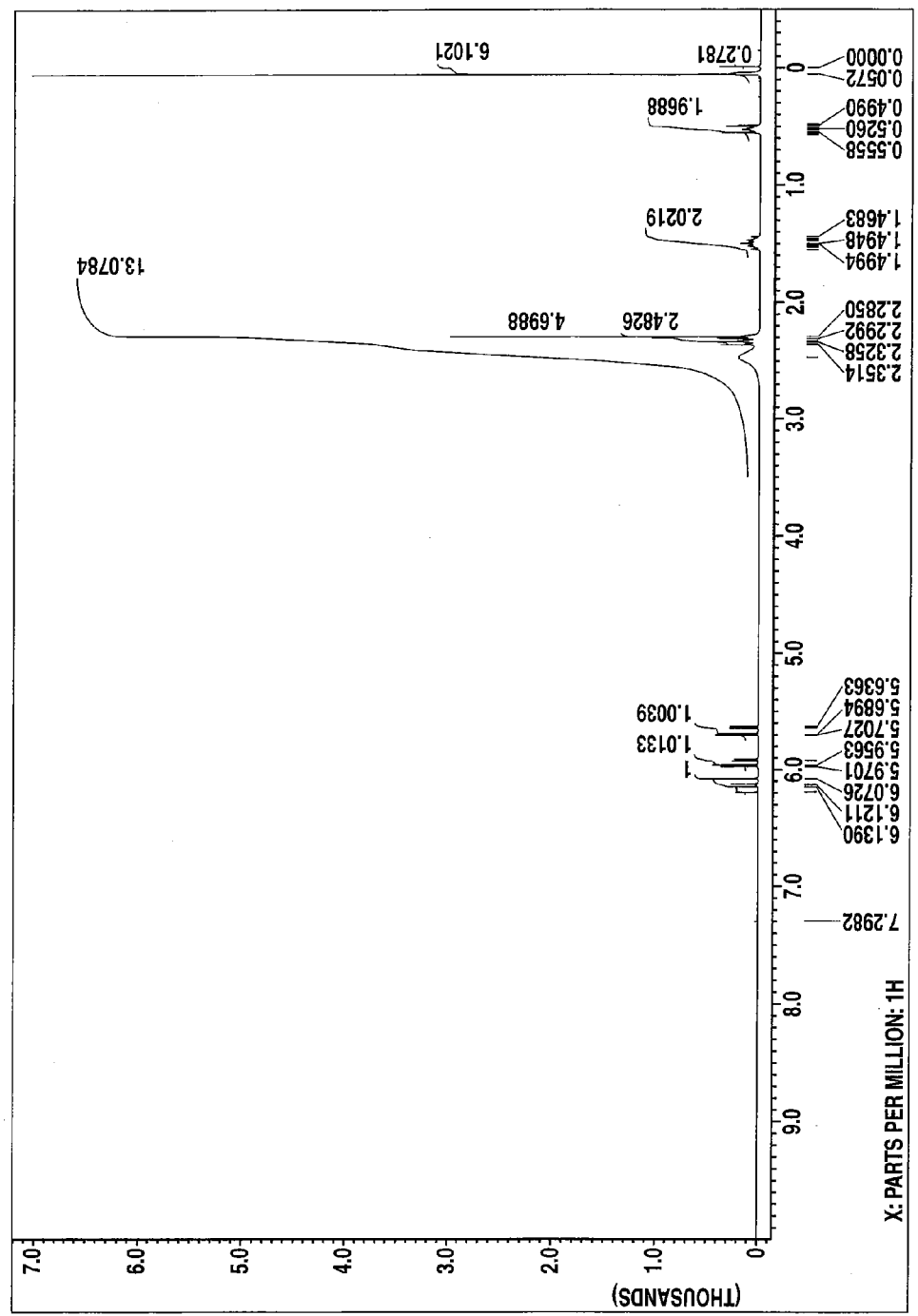
FIGS. 3 and 4 are ¹H-NMR and IR spectra of N-methylpiperazinylpropyldimethylvinylsilane in Example 2, respectively.
Figure 4:
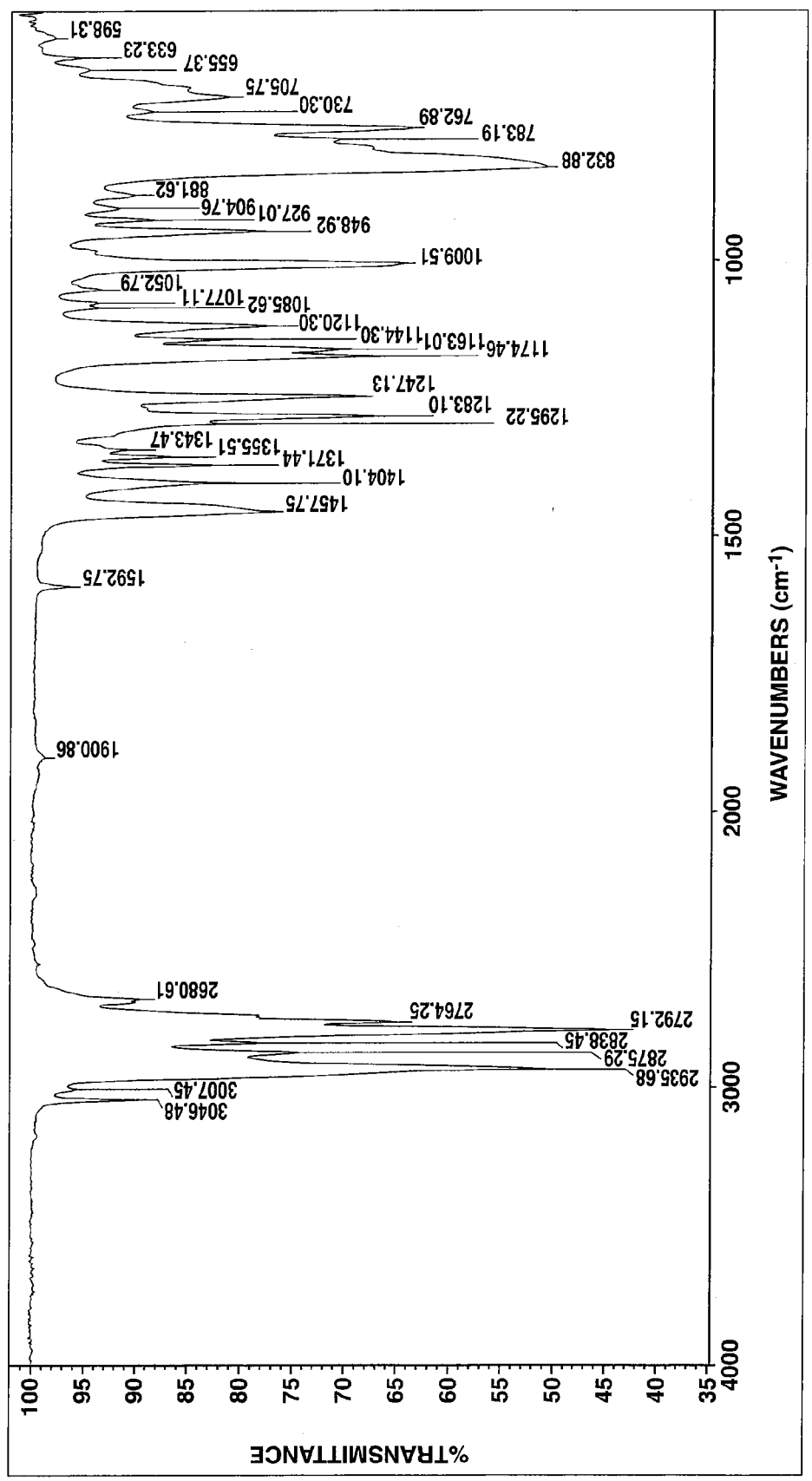

The fraction was analyzed by mass, $^1$H-NMR and IR spectrometry, with the results shown below.
Mass spectrum
m/z 226, 211, 113, 70, 42
$^1$H-NMR spectrum (in heavy chloroform)
diagram of FIG. 3
IR spectrum
diagram of FIG. 4
With these data, the compound was identified to be N-methylpiperazinylpropyldimethylvinylsilane.

Synthesis Example 2

Synthesis of bistrimethylsilylaminopropyldimethylchloro-silane
A flask equipped with a stirrer, reflux condenser, dropping funnel and thermometer was charged with 201.5 g (1.0 mol) of bistrimethylsilylallylamine and 0.7 g of a toluene solution (platinum content 3 wt %) of platinum-1,3-divinyl-1,1,3,3-tetramethyldisiloxane complex, to which 99.3 g (1.05 mol) of dimethylchlorosilane was added dropwise over 2 hours at an internal temperature of 60-70° C. The reaction solution was stirred at the temperature for 1 hour. By distillation of the reaction solution, the target compound, bistrimethylsilylaminopropyldimethylchlorosilane was collected as a fraction having a boiling point of 68° C./30 Pa in an amount of 268.0 g (yield 91%).

Example 3

Figure 5:
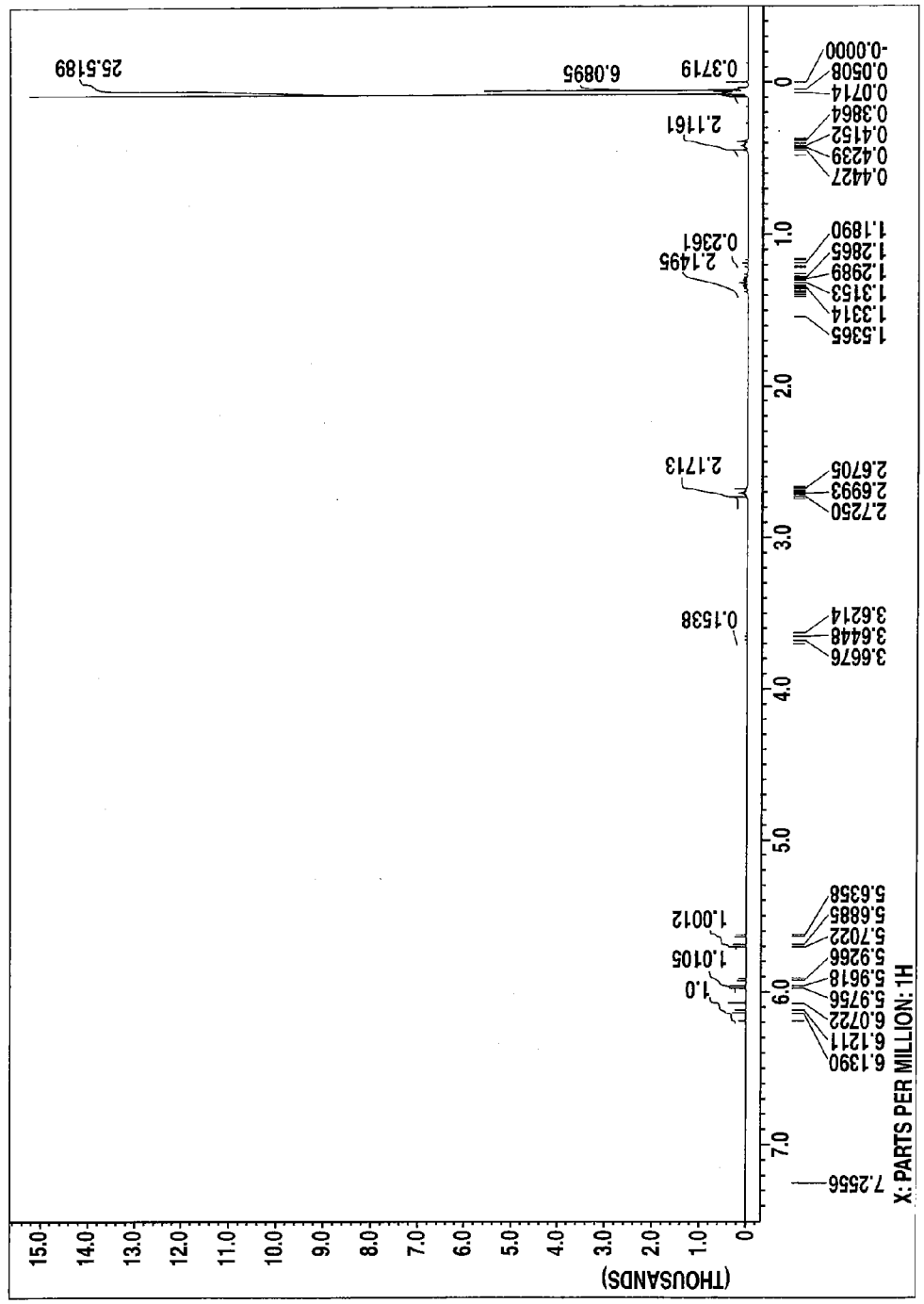

Synthesis of bistrimethylsilylaminopropyldimethylvinylsilane
A flask equipped with a stirrer, reflux condenser, dropping funnel and thermometer was charged with 53.3 g (0.18 mol) of bistrimethylsilylaminopropyldimethylchlorosilane. To the flask, 160 mL (0.22 mol) of a tetrahydrofuran solution of 1.4M vinylmagnesium chloride was added dropwise over 2 hours at an internal temperature of 60-70° C. Stirring was continued for 4 hours at the temperature. A salt formed was removed by filtration. By subsequent distillation, 40.7 g of a fraction having a boiling point of 94° C./0.4 kPa was collected.
The fraction was analyzed by mass, $^1$H-NMR and IR spectrometry, with the results shown below.
Mass spectrum
m/z 287, 272, 174, 73, 59
$^1$H-NMR spectrum (in heavy chloroform)
diagram of FIG. 5
IR spectrum
diagram of FIG. 6
With these data, the compound was identified to be bistrimethylsilylaminopropyldimethylvinylsilane.
Japanese Patent Application No. 2009-142049 is incorporated herein by reference.
Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. An amino-containing vinylsilane compound having the general formula (1):

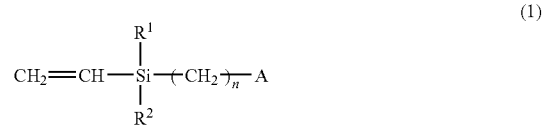

wherein $R^1$ and $R^2$ are each independently a monovalent hydrocarbon group selected from the group consisting of methyl, ethyl, propyl, isopropyl, butyl, isobutyl, sec-butyl, tert-butyl, pentyl, hexyl, heptyl, octyl, 2-ethylhexyl, nonyl, decyl, cyclopropyl, cyclobutyl, cyclopentyl, cyclohexyl and norbornyl, A is a group of the general formula (2):

wherein $R^3$ and $R^4$ are each independently a monovalent hydrocarbon group of 1 to 10 carbon atoms or triorganosilyl group of 3 to 40 carbon atoms, or the general formula (3):

wherein E is —CH$_2$—, —O— or —NR$^5$—, $R^5$ is a monovalent hydrocarbon group of 1 to 10 carbon atoms or triorganosilyl group of 3 to 40 carbon atoms, and n is an integer of 3 to 10.

2. A method for preparing the amino-containing vinylsilane compound of claim 1, comprising reacting a vinylsilane compound having the general formula (4):

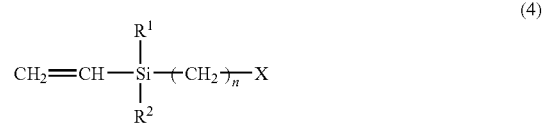

wherein $R^1$ and $R^2$ are each independently a monovalent hydrocarbon group selected from the group consisting of methyl, ethyl, propyl, isopropyl, butyl, isobutyl, sec-butyl, tert-butyl, pentyl, hexyl, heptyl, octyl, 2-ethylhexyl, nonyl, decyl, cyclopropyl, cyclobutyl, cyclopentyl, cyclohexyl and norbornyl, X is chlorine, bromine or iodine, and n is an integer of 3 to 10 with an amine compound having the general formula (5):

wherein A is a group of the general formula (2):

wherein $R^3$ and $R^4$ are each independently a monovalent hydrocarbon group of 1 to 10 carbon atoms or triorganosilyl group of 3 to 40 carbon atoms, or the general formula (3):

wherein E is —CH$_2$—, —O— or —NR$^5$—, R$^5$ is a monovalent hydrocarbon group of 1 to 10 carbon atoms or triorganosilyl group of 3 to 40 carbon atoms.

3. The method of claim 2 wherein the reaction occurs at a temperature of −20° C. to 200° C. using 1 mole of the vinylsilane compound of formula (4) and 0.5 to 5.0 moles of the amine compound of formula (5).

4. A method for preparing the amino-containing vinylsilane compound of claim 1, comprising reacting an amine compound having the general formula (6):

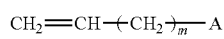  (6)

CH$_2$=CH—(CH$_2$)$_{\overline{m}}$—A wherein A is a group of the general formula (2):

—NR$^3$R$^4$  (2)

wherein R$^3$ and R$^4$ are each independently a monovalent hydrocarbon group of 1 to 10 carbon atoms or triorganosilyl group of 3 to 40 carbon atoms, or the general formula (3):

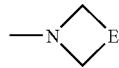  (3)

wherein E is —CH$_2$—, —O— or —NR$^5$—, R$^5$ is a monovalent hydrocarbon group of 1 to 10 carbon atoms or triorganosilyl group of 3 to 40 carbon atoms, and m is an integer of 1 to 8, with a hydrogensilane compound having the general formula (7):

HSiR$^1$R$^2$Y  (7)

wherein R$^1$ and R$^2$ are each independently a monovalent hydrocarbon group selected from the group consisting of methyl, ethyl, propyl, isopropyl, butyl, isobutyl, sec-butyl, tert-butyl, pentyl, hexyl, heptyl, octyl, 2-ethylhexyl, nonyl, decyl, cyclopropyl, cyclobutyl, cyclopentyl, cyclohexyl and norbornyl, Y is an organoxy group of 1 to 10 carbon atoms, chlorine, bromine or iodine, in the presence of a platinum catalyst, to form an amino-containing silane compound having the general formula (8):

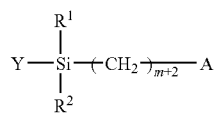  (8)

wherein R$^1$, R$^2$, A, Y and m are as defined above, and reacting the amino-containing silane compound with a vinyl Grignard reagent.

5. The method of claim 4 wherein the reaction occurs at a temperature of −20° C. to 200° C. using 1 mole of the amine compound of formula (6), 0.5 to 3.0 moles of the hydrogensilane compound of formula (7), 0.5 to 3.0 moles of the vinyl Grignard reagent, and 0.000001 to 0.01 mole of the platinum catalyst.

* * * * *